US012685640B2

(12) United States Patent
Allen et al.

(10) Patent No.: US 12,685,640 B2
(45) Date of Patent: Jul. 21, 2026

(54) REAR TIP EXTENDER HAVING MULTIPLE LOCKS FOR COUPLING WITH A PENILE PROSTHESIS

(71) Applicant: Coloplast A/S, Humlebaek (DK)

(72) Inventors: John J. Allen, Mendota Heights, MN (US); Linda Cornelius, Minneapolis, MN (US)

(73) Assignee: Coloplast A/S, Humlebaek (DK)

( * ) Notice: Subject to any disclaimer, the term of this patent is extended or adjusted under 35 U.S.C. 154(b) by 537 days.

(21) Appl. No.: 18/232,370

(22) Filed: Aug. 10, 2023

(65) Prior Publication Data

US 2024/0058130 A1     Feb. 22, 2024

Related U.S. Application Data

(60) Provisional application No. 63/398,245, filed on Aug. 16, 2022.

(51) Int. Cl.
*A61F 2/26*      (2006.01)
*A61F 2/00*      (2006.01)

(52) U.S. Cl.
CPC ........ *A61F 2/26* (2013.01); *A61F 2002/0081* (2013.01); *A61F 2220/0033* (2013.01); *A61F 2230/0071* (2013.01); *A61F 2250/0007* (2013.01); *A61F 2250/006* (2013.01)

(58) Field of Classification Search
CPC ................ A61F 2/26; A61F 2002/0081; A61F 2220/0033; A61F 2230/0071; A61F 2250/0007; A61F 2250/006; A61F 2220/0025; A61F 2002/30487; A61F 2002/30494; A61F 2002/30495; A61F 2002/305; A61F 2002/30515;

(Continued)

(56) References Cited

U.S. PATENT DOCUMENTS

| | | | | | |
|---|---|---|---|---|---|
| 4,411,260 A | * | 10/1983 | Koss | ........................ | A61F 2/26 |
| | | | | | 600/40 |
| 4,611,584 A | * | 9/1986 | Finney | ...................... | A61F 2/26 |
| | | | | | 600/40 |

(Continued)

FOREIGN PATENT DOCUMENTS

| | | | | |
|---|---|---|---|---|
| CN | 115399922 A | * | 11/2022 | ............... A61F 2/26 |
| EP | 3357458 A1 | | 8/2018 | |
| WO | 2020081366 A1 | | 4/2020 | |

OTHER PUBLICATIONS

Rigicon ® Innovative Urological Solutions (https://www.rigicon.com/inflatable-penile-prosthesis/ captured Oct. 19, 2023).

*Primary Examiner* — Brian L Casler
(74) *Attorney, Agent, or Firm* — Coloplast Corp., Coloplast A/S; Nick Baumann

(57)     ABSTRACT

An implantable penile prosthesis system has a penile implant with a proximal portion provided with an annular groove and a neck groove, and a rear tip extender forming a cavity sized to receive the proximal portion of the penile implant. The cavity of the rear tip extender is provided with a plurality of locks. The locks include a distal lock formed as an annular protrusion sized to engage with the annular groove of the penile implant and a proximal lock formed as a wedge-shaped tooth sized to engage the neck groove of the penile implant.

19 Claims, 13 Drawing Sheets

(58) Field of Classification Search
CPC .. A61F 2002/30336; A61F 2002/30345; A61F
2002/30334
USPC ........................................................ 600/40
See application file for complete search history.

(56) References Cited

U.S. PATENT DOCUMENTS

| | | | | |
|---|---|---|---|---|
| 4,628,912 | A * | 12/1986 | Fischell | A61F 2/26 600/40 |
| 5,063,914 | A * | 11/1991 | Cowen | A61F 2/26 600/40 |
| 5,067,485 | A * | 11/1991 | Cowen | A61F 2/26 600/40 |
| 6,808,489 | B2 | 10/2004 | George et al. | |
| 7,172,602 | B2 | 2/2007 | George et al. | |
| 7,648,456 | B2 | 1/2010 | Steele, Sr. | |
| 7,976,457 | B2 | 7/2011 | Steele, Sr. | |
| 9,375,314 | B2 | 6/2016 | Terlecki | |
| 9,474,610 | B2 | 10/2016 | Borgaonkar et al. | |
| 11,717,409 | B2 * | 8/2023 | DiLoreto | A61F 2/26 600/40 |
| 2003/0220539 | A1 | 11/2003 | George et al. | |
| 2011/0092764 | A1 * | 4/2011 | Harrison, Jr. | A61F 2/26 600/40 |
| 2020/0289269 | A1 | 9/2020 | Hakky | |

* cited by examiner

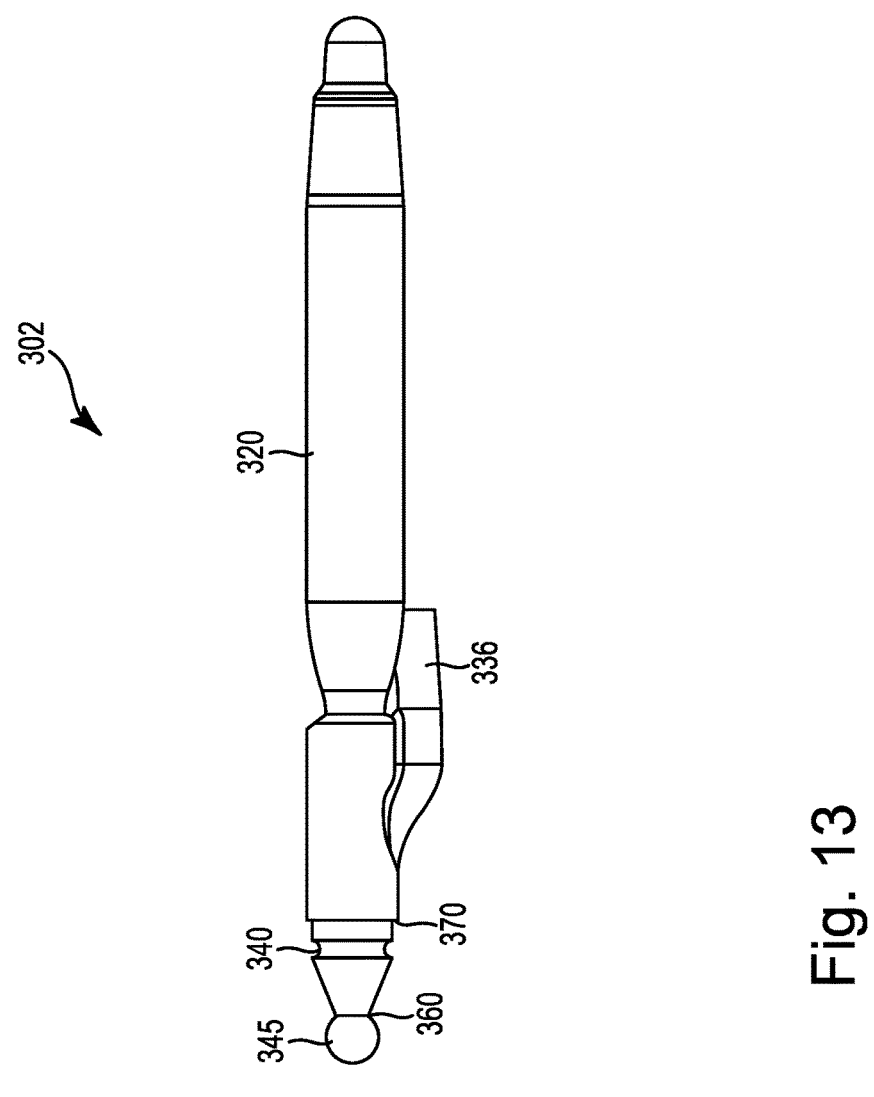
Fig. 13
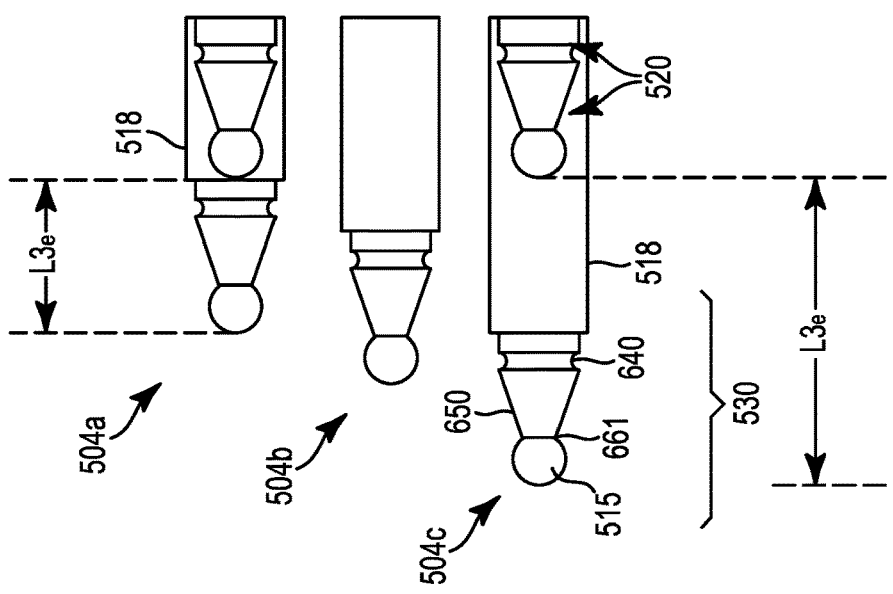

REAR TIP EXTENDER HAVING MULTIPLE LOCKS FOR COUPLING WITH A PENILE PROSTHESIS

BACKGROUND

An implanted penile prosthetic is an effective approach to relieving male erectile dysfunction.

A penile prosthesis (a device is a prosthesis prior to implant and a prosthetic after implantation) could be a malleable and non-inflatable device or an inflatable device. The malleable device has a flexible core that is bendable to various orientations, which for example allows the user to bend the penile implant to a desired erect shape or to a relaxed state. An inflatable penile prosthesis typically includes a pair of cylinders implantable in the penis, a reservoir implantable in the abdomen, and a pump implantable in the scrotum that is employed to move liquid from the reservoir into the cylinders. Pumping liquid from the reservoir to the cylinders inflates the penile implant to allow for penetrative intercourse.

Each of these penile prostheses has a portion that is implanted within the penis. The distal portion of the penile prosthesis is implanted within a dilated corpus cavernosum, and the proximal portion is implanted within a dilated crus penis. There is often a variation in the depth and width of the dilated crus penis, even within an individual patient. The surgeon desires to appropriately fit the proximal portion of the penile prosthesis within the crus and might desire to attach length-extenders to the implant to adjust for the depth of the crus penis. These length-adjusting accessories should be easy to attach yet resistant to detaching from the implant in the case of explant.

Surgeons and users would benefit from devices that improve the fit of an implantable penile prosthesis within the penis.

BRIEF DESCRIPTION OF THE DRAWINGS

The accompanying drawings are included to provide a further understanding of embodiments and are incorporated in and constitute a part of this specification. The drawings illustrate embodiments and together with the description teach principles of this disclosure. Other embodiments and the intended advantages of embodiments will be readily appreciated as they become better understood by reference to the following detailed description. The elements of the drawings are not necessarily to scale relative to each other. Like reference numerals designate corresponding similar parts.

FIG. 13 is a side view of multiple stackable rear tip extenders each suitable for attachment to each other and suitable for attachment to a penile implant.

SUMMARY

Figure 1:
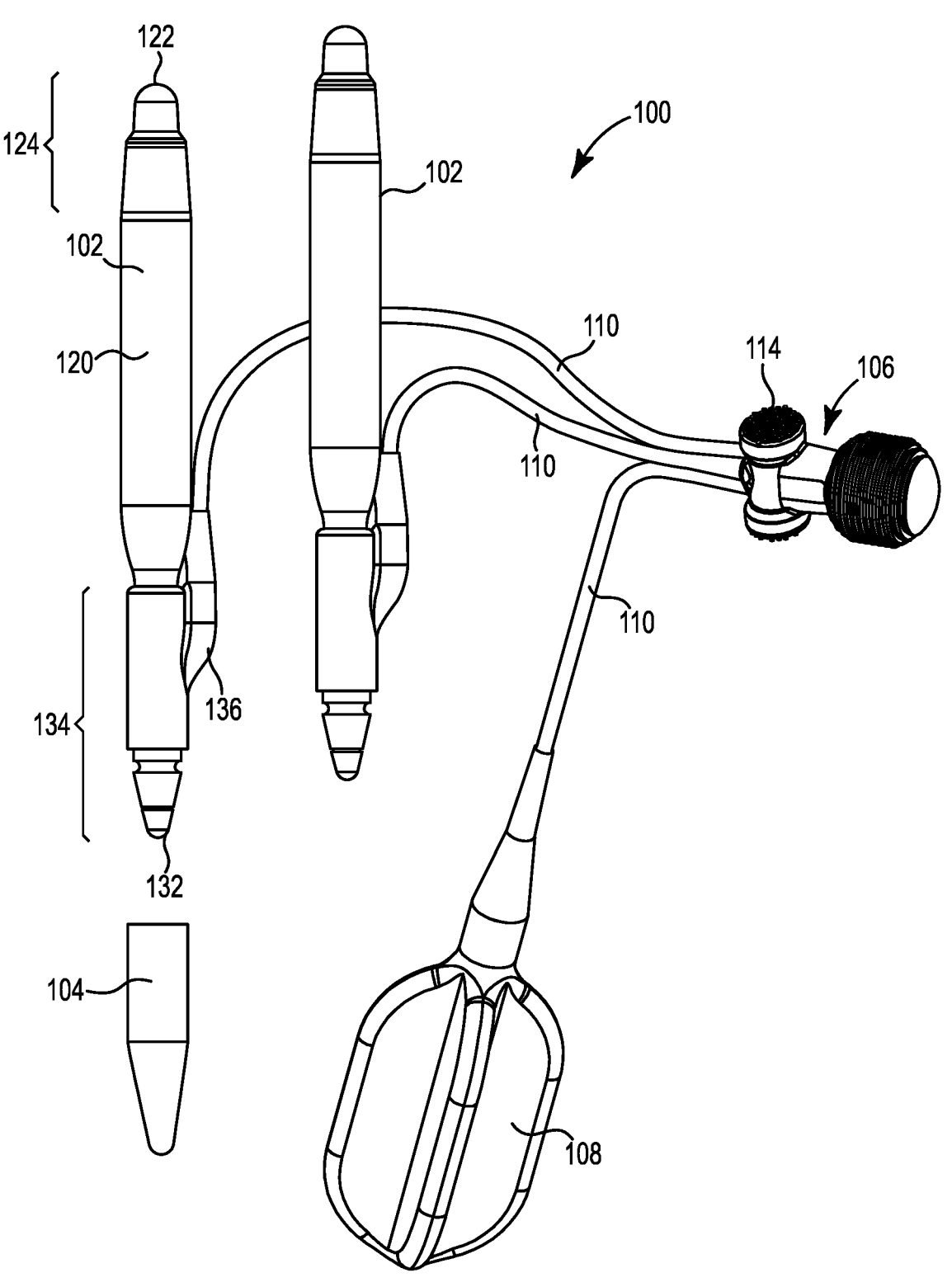
FIG. 1 is a perspective view of one embodiment of an implantable penile prosthesis system including a penile implant and a rear tip extender attachable to a proximal portion of the penile implant.

A rear tip extender for a penile prosthesis is disclosed. The rear tip extender includes multiple locks for connecting the rear tip extender over a proximal end of the penile prosthesis. The multiple locks advantageously secure the rear tip extender to the penile implant so that, in the event of a future explantation of the implant, the rear tip extender is removed along with the removal of the distal penile implant. At least one of the multiple locks on the rear tip extender mates smoothly with an exterior surface of the penile prosthesis to limit or prevent the formation of a gap or space between the rear tip extender and the penile prosthesis. The multiple locks allow the rear tip extender to maintain engagement with the prosthesis and limit gap formation between these two components even when bending forces are present during use, thus reducing or eliminating tissue ingrowth between the rear tip extender and the prosthesis over the life span of the implant, which is beneficial in case of a future explant procedure.

DETAILED DESCRIPTION

In the following Detailed Description, reference is made to the accompanying drawings, which form a part hereof, and in which is shown by way of illustration specific embodiments in which the invention may be practiced. In this regard, directional terminology, such as "top," "bottom," "front," "back," "leading," "trailing," etc., is used with reference to the orientation of the Figure(s) being described. Because components of embodiments can be positioned in different orientations, the directional terminology is used for purposes of illustration and is in no way limiting. It is to be understood that other embodiments may be utilized, and structural or logical changes may be made without departing from the scope of the present invention. The following detailed description, therefore, is not to be taken in a limiting sense.

The features of the various exemplary embodiments described in this application may be combined with each other, unless specifically noted otherwise.

The term "proximal" as employed in this application means that part that is oriented closest to a center of the human body.

The term "distal" as employed in this application means that part that is situated farthest away from the center of the human body. A distal end is the furthest endmost location of a distal portion of a thing being described, whereas a proximal end is the nearest endmost location of a proximal portion of the thing being described. As relates to penile implants, the proximal portion of the penile implant is implanted in the crus penis and the distal portion of the penile implant is implanted in the pendulous (external portion) of the penis.

The length and width of the penile prosthesis that is implanted in the distal portion of the penis is selected by the surgeon after the surgeon measures the length and girth of each dissected corpus cavernosum. Common sizes for the penile prosthesis implanted in each corpus cavernosum are characterized as "standard" or "narrow." The length of the prosthesis implanted in the crus penis may be adjusted by using one or more rear tip extenders that are attached to the proximal portion of the prosthesis.

Surgeons desire rear tip extenders that are easy to attach and resistant to detaching from the implant. Tissue will naturally grow around an implant. It is advantageous to have durable rear tip extenders that can withstand bending forces without forming a gap between the location where the rear tip extender engages the prosthesis. Reducing or avoiding the formation of the gap between the two components of the penile implant avoids eventual tissue accumulation in the gap, which could complicate a possible later explant procedure.

We describe a rear tip extender having multiple locks for coupling with a penile prosthesis. The multiple locks advantageously secure the rear tip extender to the penile implant, which in the event of a future explant, ensures the rear tip extender is removed along with the penile implant. The rear tip extender mates with the penile prosthesis in a way that prevents the formation of a gap or space between the rear tip extender and the penile implant, even if the rear tip extender experiences bending forces during use. The reduction or elimination of the gap spaces between the two components reduces or eliminates tissue ingrowth into the gap or space, which is also beneficial in the case of a future explant.

We describe a system of a rear tip extender attachable to a penile prosthesis including multiple locks that improve the resistance of the rear tip extender from removal from the penile prosthesis by double (a factor of 2 in pull-off force) over compared to the pull-off force specification for conventional rear tip extenders and penile implants. Embodiments of the system of the rear tip extender attachable to the penile prosthesis described below also reduce or eliminate separation of the rear tip extender away from the location where it is joined to the penile implant, as can sometimes occur in the presence of bending of the implant during use. The multiple locks connecting the rear tip extender to the penile prosthesis thus reduces or eliminates the formation of a gap between the components after implantation that can lead to undesirable tissue ingrowth between the components. Consequently, embodiments of the rear tip extender and penile implant system described below provide improved engagement between the rear tip extender, to reduce or eliminate tissue ingrowth between the components, and provide a system having improved explant capabilities.

One embodiment described in the application provides an implantable penile prosthesis system comprising a penile implant and a rear tip extender. The penile implant comprises a proximal portion implantable in a crus penis, with the proximal portion of the penile implant comprising: a groove formed around at least a portion of a circumference of the penile implant and having a groove diameter, a tapered section proximal the groove, with the tapered section having a continuous reduction in diameter from the groove toward a proximal-most end of the penile implant, and a neck groove formed in the tapered section between the proximal-most end of the penile implant and the groove. The groove in the proximal portion of the penile implant is referred to as an annular groove. The annular groove is a recessed area that may be suitably formed as a U-shaped groove or a C-shaped groove. Likewise, the neck groove is a recessed area and can be formed in a variety of shapes, such as in one example, a square-shaped groove with right angles. The rear tip extender forms a cavity sized to receive the proximal portion of the penile implant, with the cavity defined by an interior wall and provided with a plurality of locks comprising: a distal lock formed as an annular protrusion extending radially inward away from the interior wall of the cavity, where the annular protrusion is sized to engage with the annular groove of the penile implant, and a proximal lock formed as a wedge-shaped tooth extending radially inward away from the interior wall of the cavity, with the wedge-shaped tooth sized to engage the neck groove of the penile implant. The distal lock and the proximal lock of the rear tip extender advantageously increase the pull-off force between the rear tip extender and the penile implant by over 100% compared to the engagement between a conventional rear tip extender and its penile implant. This advantage contributes to the added benefits of reducing or eliminating tissue ingrowth between the components to provide a system having improved explant capabilities.

One aspect of the system includes an embodiment where the annular protrusion of the distal lock is sized to engage with an entire circumference of the annular groove of the penile implant, and the proximal lock comprises a plurality of wedge-shaped teeth extending radially inward away from the interior wall of the cavity. The plurality of wedge-shaped teeth is distributed around a circumference of the cavity of the rear tip extender.

One aspect of the system includes the annular protrusion of the distal lock is sized to engage with an entire circumference of the annular groove of the penile implant, and the wedge-shaped tooth of the proximal lock is sized to engage with an entire circumference of the neck groove of the penile implant.

One aspect of the system includes the proximal portion of the penile implant further comprises a step section distal the annular groove, with the step section having a step diameter that is greater than the groove diameter; wherein, when the rear tip extender is coupled to the proximal portion of the penile implant, an exterior surface of the rear tip extender smoothly transitions and is co-planar to an exterior surface of the proximal portion of the penile implant.

One aspect of the system includes a joint formed at a location where the rear tip extender is coupled to the proximal portion of the penile implant, and the plurality of locks of the rear tip extender combine to prevent formation of a gap in the joint when a bending force is applied to the system.

One aspect of the system includes the neck groove of the proximal portion of the penile implant is formed by a junction between a portion of a spherical ball attached proximal to the tapered section, and the wedge-shaped tooth is sized to engage with the junction.

One aspect of the system includes the neck groove of the proximal portion of the penile implant is formed by a junction between a portion of a spherical ball attached proximal to the tapered section, and a diameter of the portion of the spherical ball is larger than a smallest diameter of the tapered section.

One aspect of the system includes the cavity of the rear tip extender includes a section of a spherical cavity located proximal to the wedge-shaped tooth and sized to receive the portion of the spherical ball.

One aspect of the system includes the penile implant is an inflatable penile implant attachable to a liquid reservoir and a pump by tubing.

One aspect of the system includes the proximal portion of the penile implant further comprises a first sphere that forms the proximal-most end of the penile implant and the neck groove of the penile implant is formed at a junction between the first sphere and the tapered section.

One aspect of the system includes the cavity of the rear tip extender is formed to include a spherical cavity sized to receive the first sphere of the proximal portion of the penile implant, and the wedge-shaped tooth of the proximal lock on the interior wall of the rear tip extender is formed by a surface of the spherical cavity and is adapted to engage the junction located between the first sphere and the tapered section.

One aspect of the system includes the rear tip extender further comprises a second sphere that forms a proximal-most end of the rear tip extender.

One aspect of the system includes the rear tip extender comprises a stackable rear tip extender (RTE), with an exterior wall of the stackable RTE comprising: an annular RTE groove formed around a circumference of the stackable RTE, a tapered RTE section proximal the annular RTE groove, with the tapered RTE section having a continuous reduction in diameter from the annular RTE groove toward the second sphere at the proximal-most end of the stackable RTE, and a neck RTE groove formed in the tapered RTE section at a junction between the second sphere and the tapered RTE section.

One aspect of the system further includes a plurality of the stackable RTEs, with the exterior wall of each of the plurality of the stackable RTEs comprising the annular RTE groove, the tapered RTE section, and the neck RTE groove.

One aspect of the system includes each one of the plurality of the stackable RTEs has a length that is different from a length of another one of the plurality of the stackable RTEs.

One aspect of the system includes the rear tip extender comprises a non-stackable rear tip extender (RTE), with an exterior wall of the non-stackable RTE comprising: a cylindrical section extending from a distal end of the non-stackable RTE in a direction toward the proximal-most end of the non-stackable RTE, a tapered RTE section proximal the cylindrical section, with the tapered RTE section having a continuous reduction in diameter from the cylindrical section to the second sphere at the proximal-most end of the non-stackable RTE, and a neck RTE groove formed in the tapered RTE section at a junction of the second sphere and the tapered RTE section.

One aspect of the system further includes a plurality of the non-stackable RTEs.

One aspect of the system includes each one of the plurality of the non-stackable RTEs has a length of the cylindrical section that is different from a length of the cylindrical section of another one of the plurality of the non-stackable RTEs.

FIG. 1 is a perspective view of one embodiment of an implantable penile prosthesis system 100. The system 100 includes a penile implant 102 implantable into each corpus of the penis and a rear tip extender 104 (RTE 104) attachable to the penile implant 102. The RTE 104 advantageously allows a surgeon to adjust the length of the portion of the penile implant 102 that is implanted in the crus penis. One RTE 104 is shown since the surgeon decides which size of RTE 104 to attach to each one of the implants 102.

The implantable penile prosthesis system 100 includes a pump 106 attached or attachable between the penile implants 102 and a reservoir 108, for example with suitable tubing 110 connected between the pump 106 and the implants 102 and other like tubing 110 connected between the pump 106 and the reservoir 108.

The pump 106 is provided to move liquid out from the reservoir 108 and into the penile implants 102. One embodiment of the pump 106 includes a pump bulb, where squeezing of the pump bulb moves the liquid from the reservoir 108 into the implants 102. The displaced liquid remains under pressure within the implants 102 to provide the implants with a rigidity sufficient for penetrative intercourse. A release pad 114 is provided on the pump 106 and pressing the release pad 114 displaces a valve stem inside the pump 106 to allow the pressurized liquid to return from the penile implants 102 back to the reservoir 108. One suitable pump 106 is available from Coloplast Corp., Minneapolis, Minnesota as part of an erectile dysfunction treatment product sold under the registered trademark TITAN penile prosthesis.

The reservoir 108 is sized to maintain a volume of liquid between about 50-300 ml. In one embodiment, the reservoir 108 is provided as a "cloverleaf" style of reservoir having multiple leaves that may be folded one against the other to compact the reservoir 108 for implantation into the abdomen of the user. One suitable reservoir 108 is sized to retain approximately 130 mL of liquid and is available from Coloplast Corp., Minneapolis, Minnesota.

The RTE 104 is suitable for use with a malleable (or, not inflatable) penile implant or with an inflatable penile implant. The embodiment of the penile implant shown in FIG. 1 is an inflatable penile implant, which is inflatable with liquid from the reservoir 108 to achieve a stiffness suitable for penetrative intercourse. Each of the penile implants 102 include an inflatable cylinder 120 extending from a distal end 122 of a distal portion 124 of the implant 102 to a rear portion of the implant 102. The rear portion of the implant 102 includes a proximal-most end 132 located on a proximal portion 134 of the penile implant 102. A connection tube 136 is connected to the proximal portion 134 of the penile implant 102, where the connection tube 136 is adapted to couple with the tubing 110 and provide a level of strain relief for the implant 102.

The proximal-most end 132 (with or without the rear tip extender 104) is implanted in the crus of the penis and the distal end 122 is implanted within the glans penis. The inflatable cylinders 120 are fabricated from material configured to collapse when the cylinders 120 are deflated to provide the penis with a flaccid state and expand (like a balloon) when the cylinders 120 are inflated with liquid to provide the penis with an erection. As a point of reference, the cylinders 120 are illustrated in an inflated state. Suitable material for fabricating the cylinders 120 includes silicone, biocompatible polymers such as urethanes, blends of polymers with urethane, copolymers of urethane, or the like.

Figure 2:
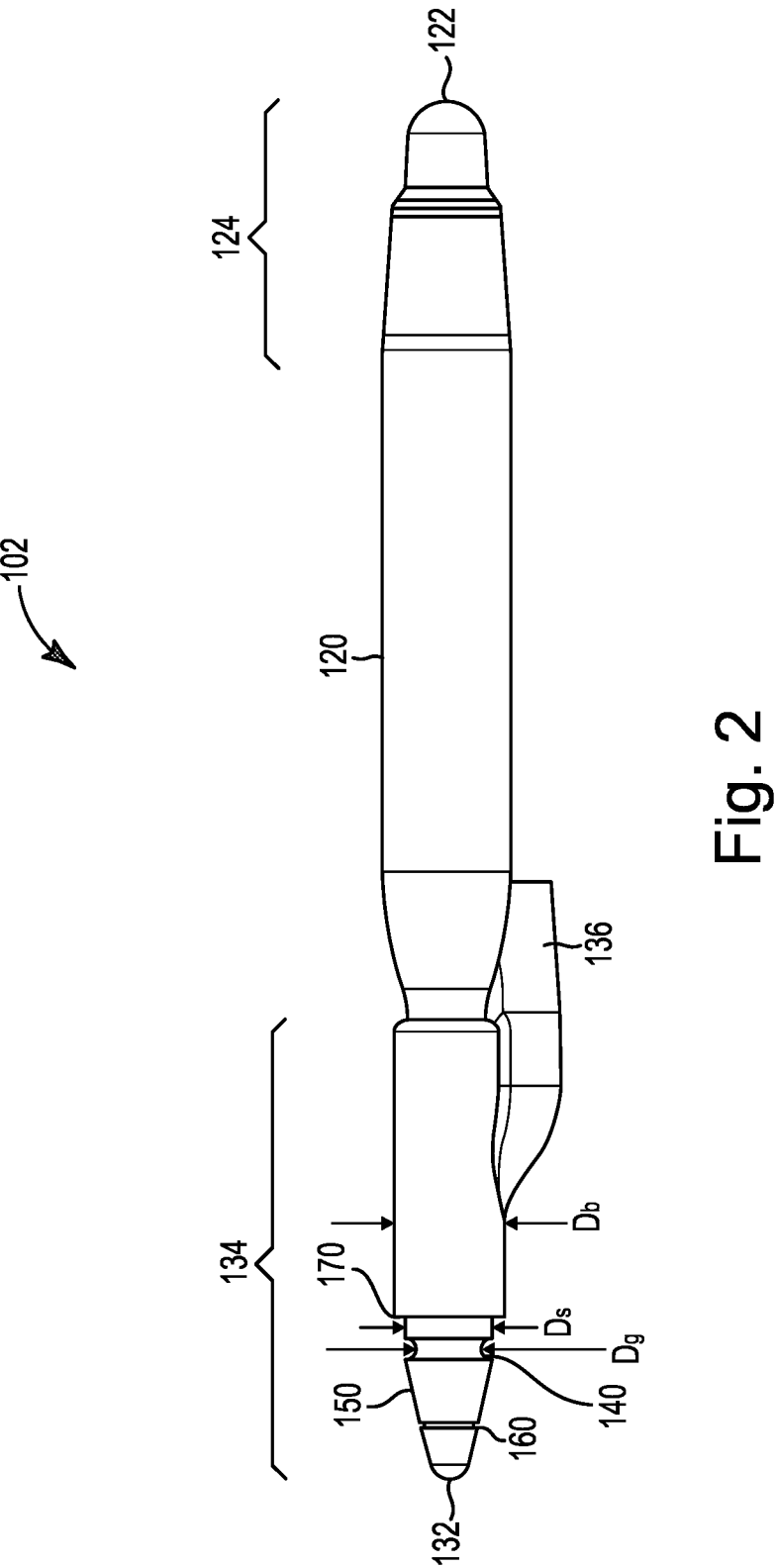
FIG. 2 is a side view of the penile implant.

FIG. 2 is a side view of one embodiment of the penile implant 102. The penile implant 102 extends from the distal end 122 of the distal portion 124 of the implant 102 that is ultimately implanted into the distal part of the penis (the glans penis) to the proximal-most end 132 of the proximal portion 134 of the implant 102 that is ultimately implanted into the proximal part of the penis (the crus penis). The connection tube 136 is connected to the proximal portion 134 of the penile implant 102 and communicates internally with the inflatable cylinder 120.

The proximal portion 134 of the penile implant 102 is configured and adapted to couple with the RTE 104. The proximal portion 134 includes an annular groove 140 formed around a circumference of the penile implant 102, where the annular groove 140 is formed (for example by molding or machining) to have a groove diameter Dg. A tapered section 150 is formed proximal the annular groove 140, with the tapered section 150 having a reduction in diameter from the annular groove 140 toward the proximal-most end 132 of the penile implant 102. The illustrated embodiment provides a continuous reduction in diameter for the tapered section 150 from the annular groove 140 toward the proximal-most end 132, although other diameter reduction structures are acceptable. A neck groove 160 is formed in the tapered section 150 between the proximal-most end 132 of the penile implant 102 and the annular groove 140. A step section 170 is formed distal the annular groove 140, and the step section 170 is formed to have a step diameter Ds that is greater than the groove diameter Dg and less than a diameter Db of the base of the penile implant 102. The step section 170 and the step diameter Ds allow a smooth transition from the base of the penile implant 102 to the RTE 104.

The annular groove 140 is a recessed area that may be suitably formed as a U-shaped groove or a C-shaped groove. The neck groove 160 is a recessed area and can be formed in a variety of shapes, such as a U-shaped groove, a C-shaped groove, or a square-shaped groove with right angles.

The annular groove 140 and the neck groove 160 of the implant 102 provide engagement locations that allow durable connection with the RTE 104. In a complementary manner, the RTE 104 is provided with a plurality of locks that engage with the annular groove 140 and the neck groove 160 of the implant 102, which is described in greater detail below. The plurality of locks on the RTE 104 and the multiple engagement locations 140, 160, 170 on the proximal portion 134 of the penile implant 102 combine to provide a durable lock between the two components that resist separation of the RTE 104 from the implant 102, even during an explant procedure.

Figure 3:
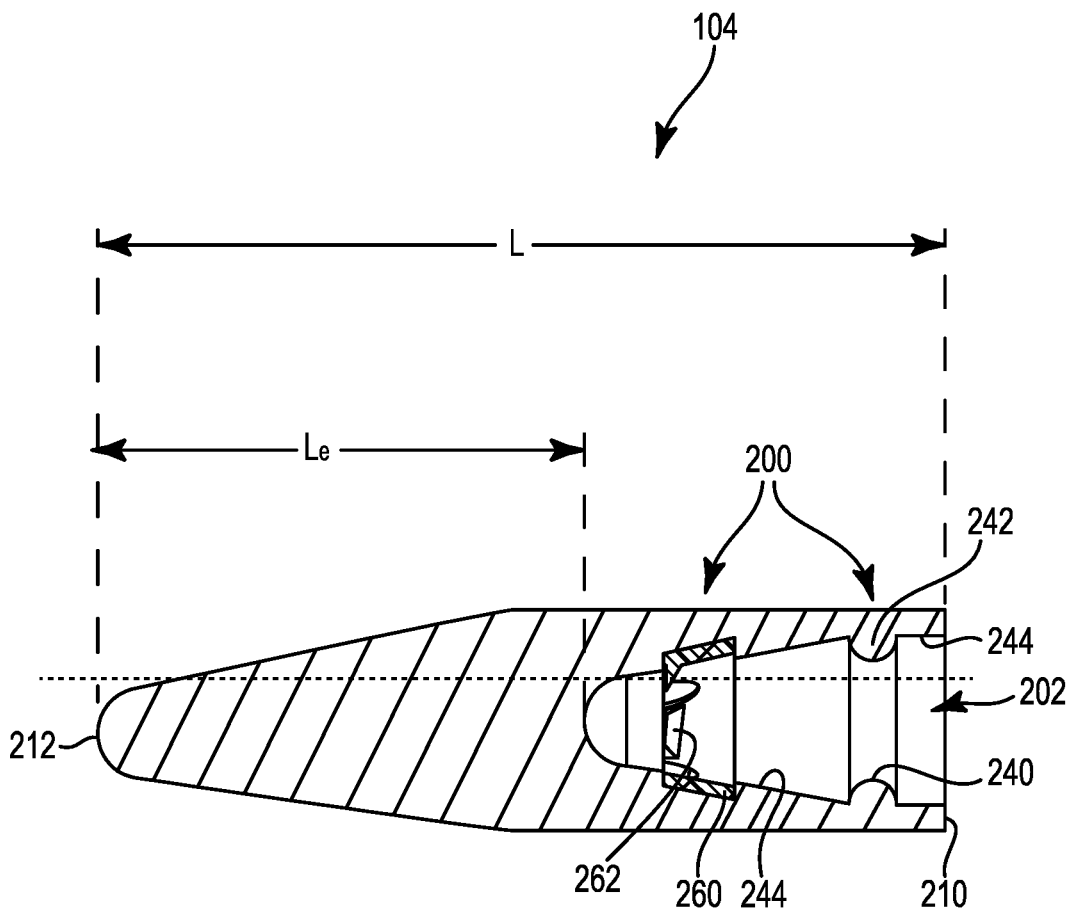
FIG. 3 is a cross-sectional view of the rear tip extender.

FIG. 3 is a cross-sectional view of the rear tip extender 104. Embodiments of the rear tip extender 104 provide a plurality of locks 200 within a cavity 202 of the RTE 104 that cooperate with the grooves 140, 160 of the implants 102 to secure the RTE 104 to the implant 102. The locks 200 combine to durably hold the rear tip extender 104 in place on the implant 102 in a way that beneficially resists separation, for example if the implant 102 is explanted years after implantation.

The RTE 104 extends a length L between a distal end 210 and a proximal end 212. When the RTE 104 is coupled to the penile implant 102 (FIG. 2), the RTE 104 provides an added effective length Le to the penile implant 102, where the added effective length Le is measured from a proximal end of the cavity 202 to the proximal end 212 of the RTE 104.

A variety of RTEs 104 may be provided with each RTE 104 having a different length L and a different added effective length Le. Surgeons have indicated a preference to have a selection of RTEs 104 available at the time of surgery and we describe RTEs 104 provided in increasing sizes of 0.5 cm increments (for example, a selection of RTEs with lengths Le sized from 1.0 cm, 1.5 cm, 2.0 cm, 2.5 cm, to 3.0 cm, etc.). In one embodiment, the RTE 104 is a three-dimensional conical body and includes a tapered diameter that tapers from a larger diameter at the distal end 210 to a smaller diameter at the proximal end 212. The taper may be linear or a combination of non-tapered and tapered sections, as shown in FIG. 3. One suitable material for fabricating the RTE 104 is silicone, for example a liquid silicone rubber, of a durometer between 50 A-70 A Shore hardness.

The plurality of locks 200 include a distal lock 240, a proximal lock 260, and a cavity lock formed by the interior wall 244 of the cavity 202 at the distal end 210 that mates with the step section 170.

The distal lock 240 is formed as an annular protrusion 242 extending radially inward away from the interior wall 244 of the cavity 202. The annular protrusion 242 is sized to engage in a complementary way with the annular groove 140 (FIG. 2) of the penile implant 102.

The proximal lock 260 is formed as a plurality of wedge-shaped teeth 262 extending radially inward away from the interior wall 244 of the cavity 202, where the wedge-shaped teeth 262 are sized to engage the neck groove 160 (FIG. 2) of the penile implant 102. The proximal lock 260 may be suitably molded as an integral part of the RTE 104 or may be an insert placed and retained inside of the cavity 202 of the RTE 104. If the proximal lock 260 is an insert into the RTE 104 it is permanently connected to the RTE 104 using adhesives or chemical or mechanical bonding.

The cavity lock on the distal end 210 is provided to ensure the RTE 104 mates smoothly with the implant, and the mating of the cavity lock with the step section 170 (FIG. 2) prevents tissue ingrowth at the mating location and resists bending forces from separating the RTE 104 from the proximal portion 134 of the implant 102.

Figure 4:
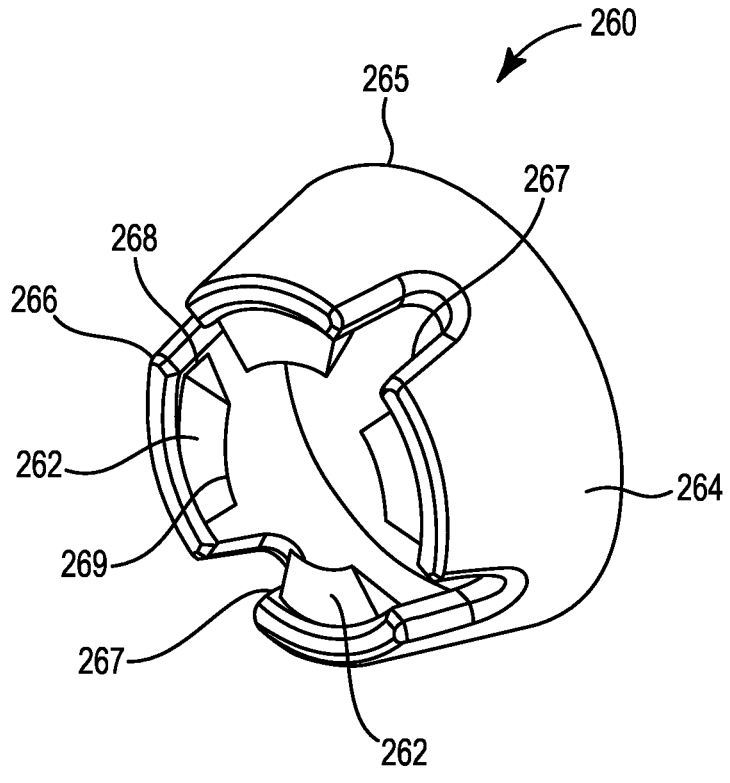
FIG. 4 is a perspective view of one embodiment of a proximal lock of the rear tip extender, with the proximal lock including a plurality of teeth.

FIG. 4 is a perspective view of one embodiment of the proximal lock 260 provided in the form of an insert 264 insertable or moldable into the rear tip extender 104. The proximal lock 260 includes a plurality of the wedge-shaped teeth 262 distributed around a circumference of the insert 264.

In one embodiment, the insert 264 tapers from a larger diameter at a distal end 265 to a smaller diameter at a proximal end 266 and includes multiple recesses 267 formed in the proximal end 266. The recesses 267 allow the insert 264 to flex as the proximal portion 134 (FIG. 2) of the implant 102 is inserted into the RTE 104, which ensures that the wedge-shaped teeth 262 firmly engage with the neck groove 160 of the implant (FIG. 2). The plurality of the wedge-shaped teeth 262 are uniformly distributed around the perimeter of the proximal end 266 and are directed radially inward on the insert 264. Each of the wedge-shaped teeth 262 have a base 268 that is wider than a pointed end 269 of the wedge-shaped tooth. The pointed edge 269 of each of the wedge-shaped teeth 262 is adapted to insert into and engage with the neck groove 160 of the implant 102 at four locations around the proximal portion 134 (FIG. 2) of the implant 102.

Figure 5:
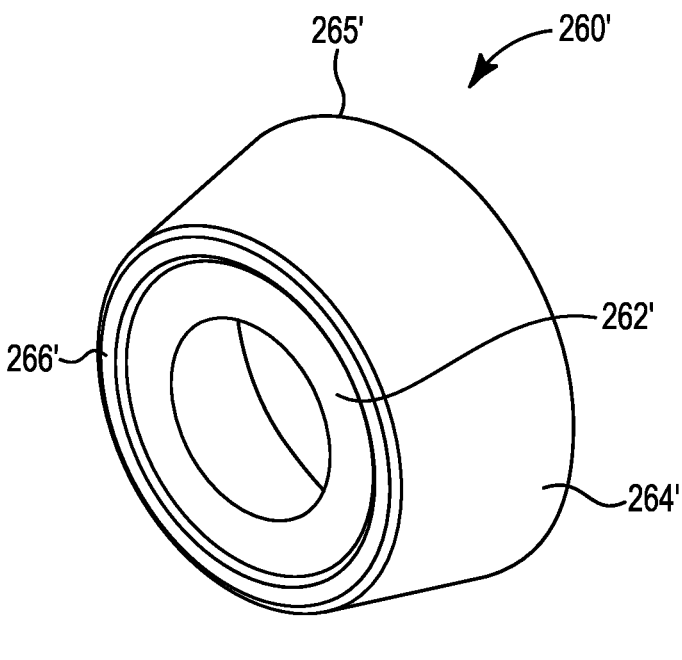
FIG. 5 is a perspective view of one embodiment of a proximal lock of the rear tip extender, with the proximal lock including an annular tooth.

FIG. 5 is a perspective view of another embodiment of a proximal lock 260' in the form of an insert 264' that is insertable into the RTE 104. The proximal lock 260' is provided with a single wedge-shaped tooth 262' extending around the circumference of the insert 264'. The insert 264' tapers from a larger diameter at a distal end 265' to a smaller diameter at a proximal end 266'. The tooth 262' is located at the proximal end 266' and extends radially inward toward a center of the insert 264'. The pointed edge of the wedge-shaped tooth 262' is adapted to insert into, for example by flexing, and engage around an entire circumference of the neck groove 160 of the implant 102.

Figure 6:
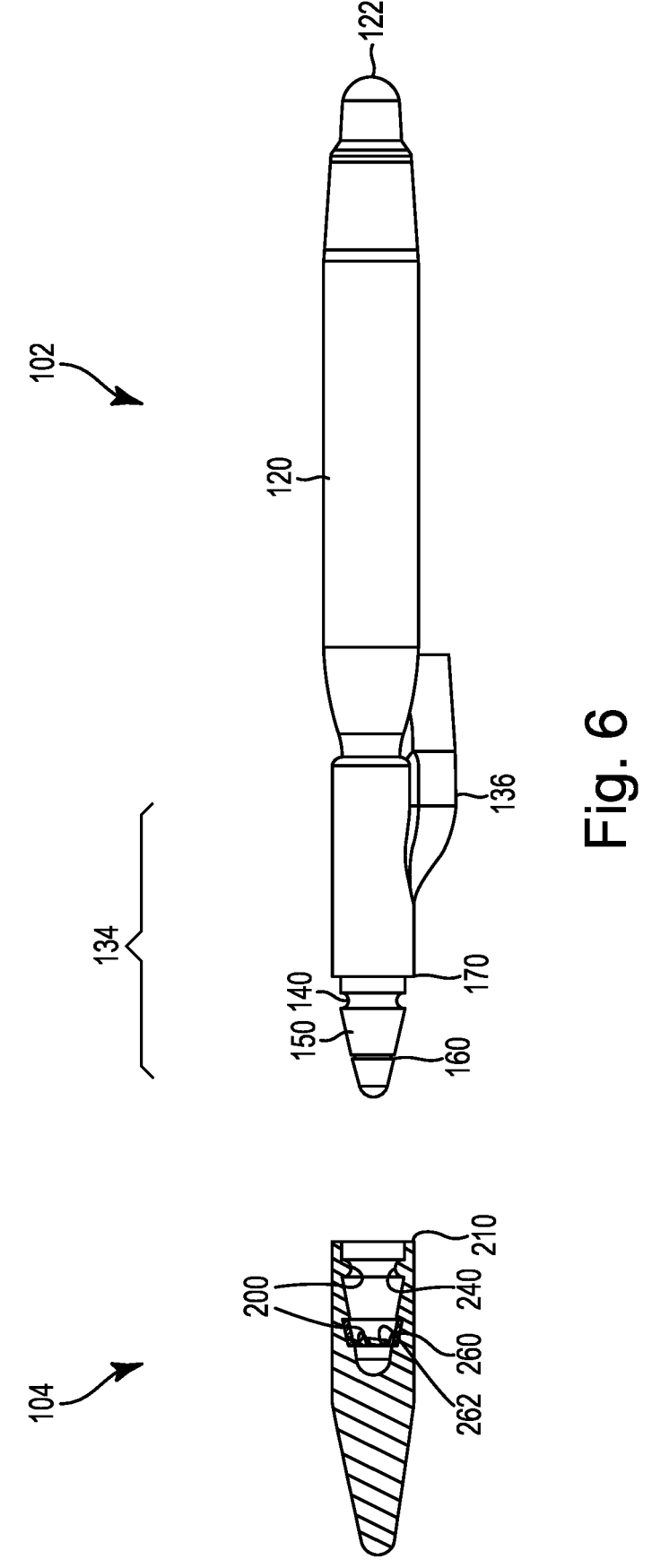
FIG. 6 is a side view of one embodiment of the rear tip extender of FIG. 3 positioned for attachment to the penile implant of FIG. 2.
Figure 7:
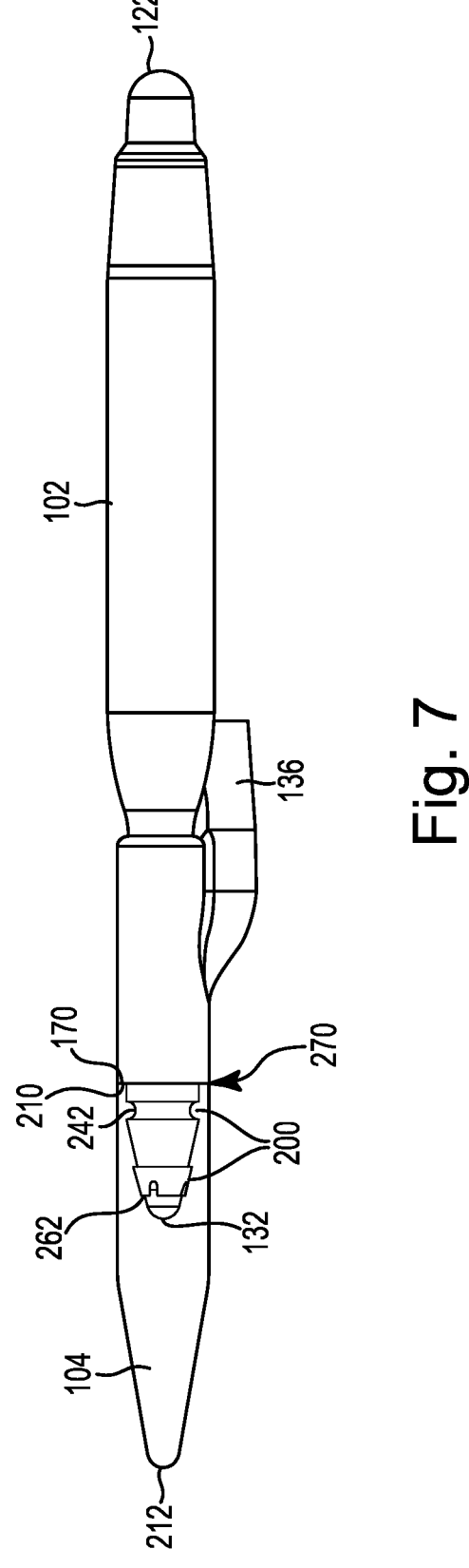
FIG. 7 is a side view of the rear tip extender connected to the penile implant.
Figure 8:
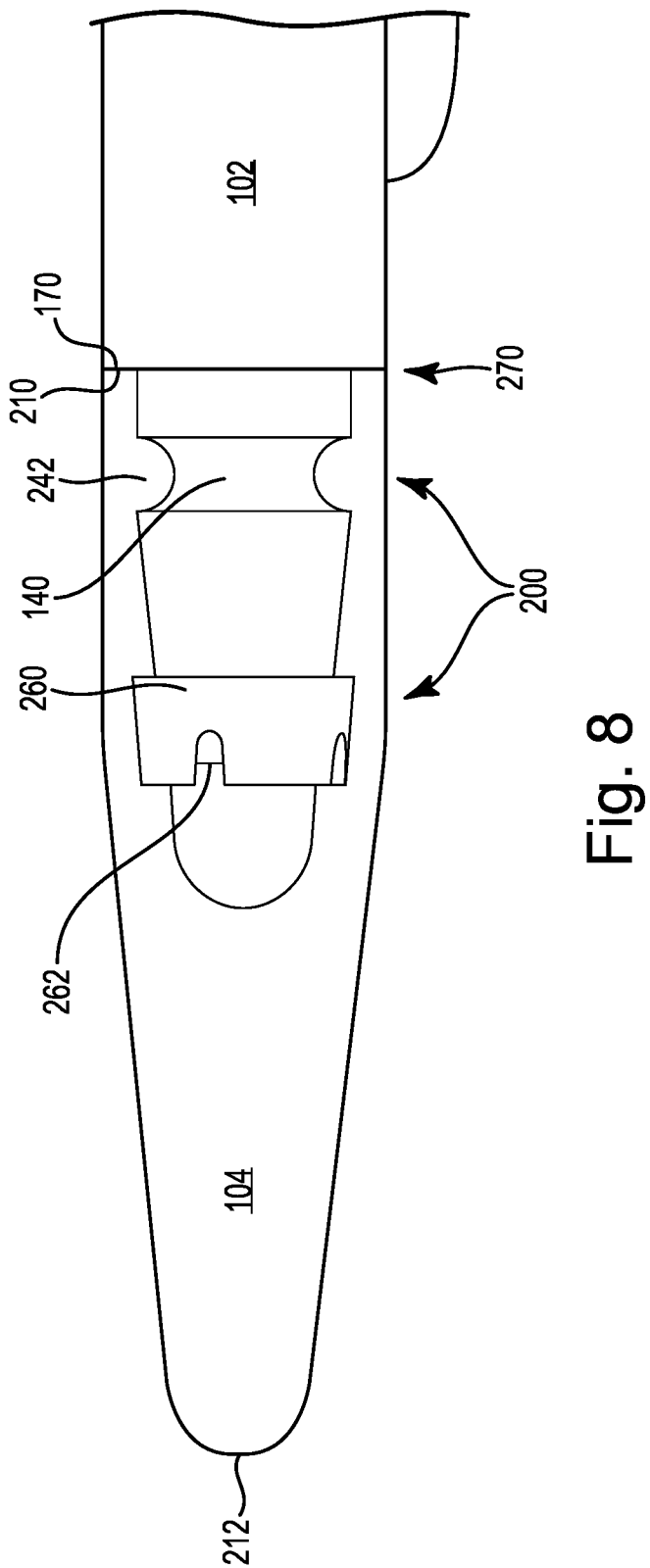
FIG. 8 is a schematic view of a plurality of locks of the rear tip extender engaged with the proximal portion of the penile implant.

FIG. 6 is a side view of the RTE 104 positioned for attachment to the penile implant 102, FIG. 7 is a side view of the RTE 104 connected with the penile implant 102, and FIG. 8 is a schematic view of the plurality of locks 200 securing the RTE 104 to the penile implant 102.

The surgeon usually measures the depth and width of the crus penis and the length of the distal (or external) penis before selecting a penile implant 102. If the surgeon determines that the length of the implant should be increased, the surgeon will select a suitable sized RTE 104 and connect it to the implant 102.

FIG. 6 illustrates alignment of the RTE 104 prior to engagement with the implant 102. The long axis of the RTE 104 is aligned with the long axis of the implant 102 such that the distal lock 240 of the RTE 104 is oriented for engagement with the annular groove 140 of the implant 102 and the proximal lock 260 is oriented for engagement with the neck groove 160 of the implant 102. FIG. 6 illustrates a typical alignment prior to the surgeon pressing the RTE 104 and the implant 102 together, where the press fitting can be aided by rotating or twisting the components relative to each other.

FIG. 7 and FIG. 8 provide two views of the plurality of locks 200 of the RTE 104 connected to the implant 102. The annular protrusion 242 of the distal lock 240 of the RTE 104 is mated with the complementary annular groove 140 of the implant 102, the wedge-shaped teeth 262 (FIG. 8) of the proximal lock 260 are mated with the complementary neck groove 160 of the implant 102, and the distal end 210 of the RTE engages with the step section 170 of the implant 102. As connected, the effective length of the implant is increased by the addition of the RTE 104.

FIG. 8 illustrates the uniform coupling of the RTE 104 to the implant 102 without a gap or space between the two components. The distal end 210 of the RTE 104 is structured to both engage and mate with the step section 170 of the implant 102 such that the exterior surface of the RTE 104 smoothly transitions and is co-planar to the exterior surface of the proximal portion 134 of the penile implant 102. A joint 270 or an abutment 270 is formed at a location where the distal end 210 of the RTE 104 meets the step section 170 of the implant 102. The plurality of locks 200 of the RTE 104 and the implant 102 combine to prevent the formation of a gap in the joint 270 when a bending force is applied to the implanted system 100 (FIG. 1). The absence of a gap at the joint 270 between the RTE 104 and the implant 102, even under a bending load, prevents tissue ingrowth at that area of the system. The reduced or eliminated tissue ingrowth at the joint 270 improves the structural integrity of the implanted implant 102/RTE 104 to provide for efficient and effective explant of the implant 102 if the surgeon decides that is the proper eventual course of action.

Suitable dimensions for the RTE 104 are provided as an example. One suitable RTE 104 provides an added effective length Le of 2.0 cm when attached to the implant 102. As noted above, a variety of RTEs 104 would typically be provided in a kit to accommodate adding an effective length Le (FIG. 3) to the penile implant in increments of 0.5 cm. The proximal end 212 of the RTE 104 has a tip radius of 2.0 mm. The distal end 210 of the RTE 104 has an outside diameter of about 10 mm and is selected to smoothly match a diameter of the implant 102 measured at the step section 170. Thus, the RTE diameter measured at the distal end 210 is selected to match the diameter of the proximal end portion 134 of the implant 102, which can vary depending on whether the implant 102 is selected to be of a "narrow" size or a wider "standard" size.

The plurality of locks 200 of the RTE 104 and the implant 102 combine to resist pull-off of the RTE 104 from the implant 102 during an explant procedure. The prior style of rear tip extenders can, under some circumstances, be pulled-off its implant in response to a longitudinal pulling force of less than about 3 pounds force (less than about 13.4 Newtons). In a marked contrast, the plurality of locks 200 of the RTE 104 and the implant 102 improve the pull-off force by combining to resist a longitudinal pulling force in a range from about 4 pounds force to about 8 pounds force (in a range from about 17.5 Newtons to about 35 Newtons), which is an improvement in pull-off force for the RTE 104 over the prior rear tip extender by between 133% and 266%.

Figure 9:
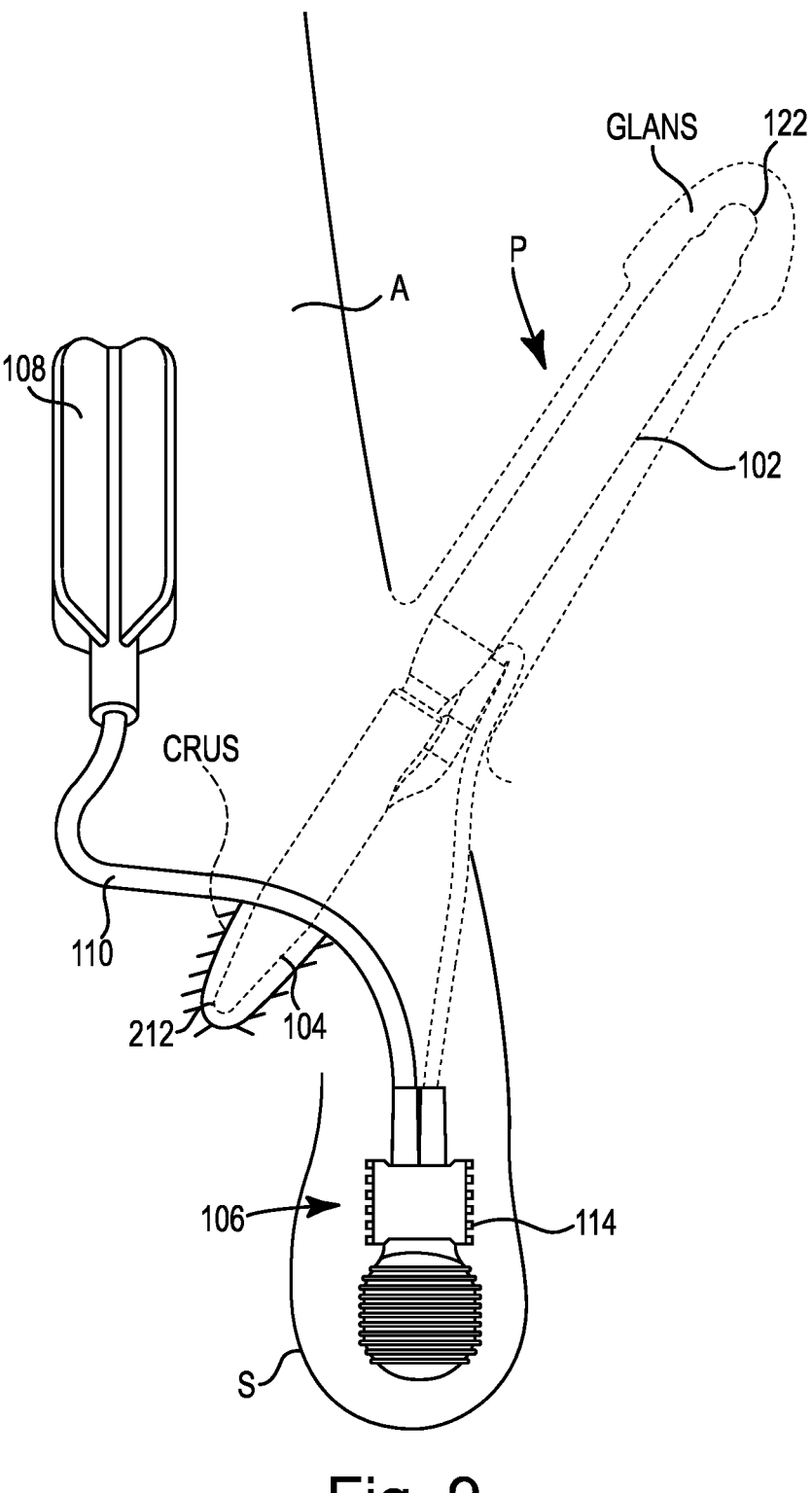
FIG. 9 is a schematic view of the system of FIG. 1 implanted in a patient.

FIG. 9 is a schematic view of the system 100 implanted in a patient.

The groin area of the patient is shaved, antiseptically cleaned, for example with a surgical solution, and draped with a sterile drape. A retraction device, such as a surgical retractor sold under the trademark Lone Star and available from Lone Star Medical Products of Stafford, TX, is placed around the penis P. Thereafter, the surgeon forms an incision to access the corpora cavernosa of the patient, where suitable examples of incisions include either an infrapubic incision or a scrotal incision. The infrapubic incision is initiated between the umbilicus and the penis (i.e., above the penis), whereas the transverse scrotal incision is made across an upper portion of the patient's scrotum S. As an example of the transverse scrotal approach, the surgeon forms a 2-3 cm transverse incision through the subcutaneous tissue of the median raphe of the upper scrotum S and dissects down through the Dartos fascia and Buck's fascia to expose the tunicae albuginea of the penis P. Thereafter, each corpus cavernosum is exposed in a corporotomy where a small (approximately 1.5 cm) incision is formed to allow the surgeon to access and subsequently dilate each corpus cavernosum. The surgeon typically will insert an instrument (such as a blunt-ended scissors or other elongated tool) to separate a portion of the spongiosum material to open a path that allows insertion of a device to measure the proximal and distal length of each corpus cavernosum. Thereafter, each corpus cavernosum is dilated distally with a suitable expanding tool to create a space for the implant 102. In one approach, the surgeon begins dilation of the penis by introducing an 8 mm dilator into the spongy tissue of the corpora and the crus with sequential progression to about a 14 mm dilator, each of which are introduced and pushed distally toward the glans penis and then proximally toward the crus of the penis, respectively. After suitable dilation of the space within the penis, the surgeon selects an implant 102 and adjusts the effective length by selecting an appropriately sized RTE 104.

The surgeon inserts and directs the distal end 122 of each of the cylindrical the implants 102 into the distal-most portion of each corpus cavernosum. The proximal end 212 of the RTE 104 is implanted into each of the dilated proximal crus penis. The corporotomy is closed, and the remaining portions of the pump 106 and the reservoir 108 of the system 100 are implanted in the scrotum S and the abdomen A, respectively, of the patient.

The RTE 104 advantageously provides the surgeon with options in adjusting the effective length of the implant 102. The locks 200 combine to secure the RTE 104 to the implant 102 in a way that resists the formation or opening of a gap at the joint 270 between the step section 170 and the distal end 210 of the RTE, particularly during bending or other stresses realized by the system 100 during use. Consequently, the RTE 104 remains durably connected to the implant 102 even if explanted.

Figure 10:
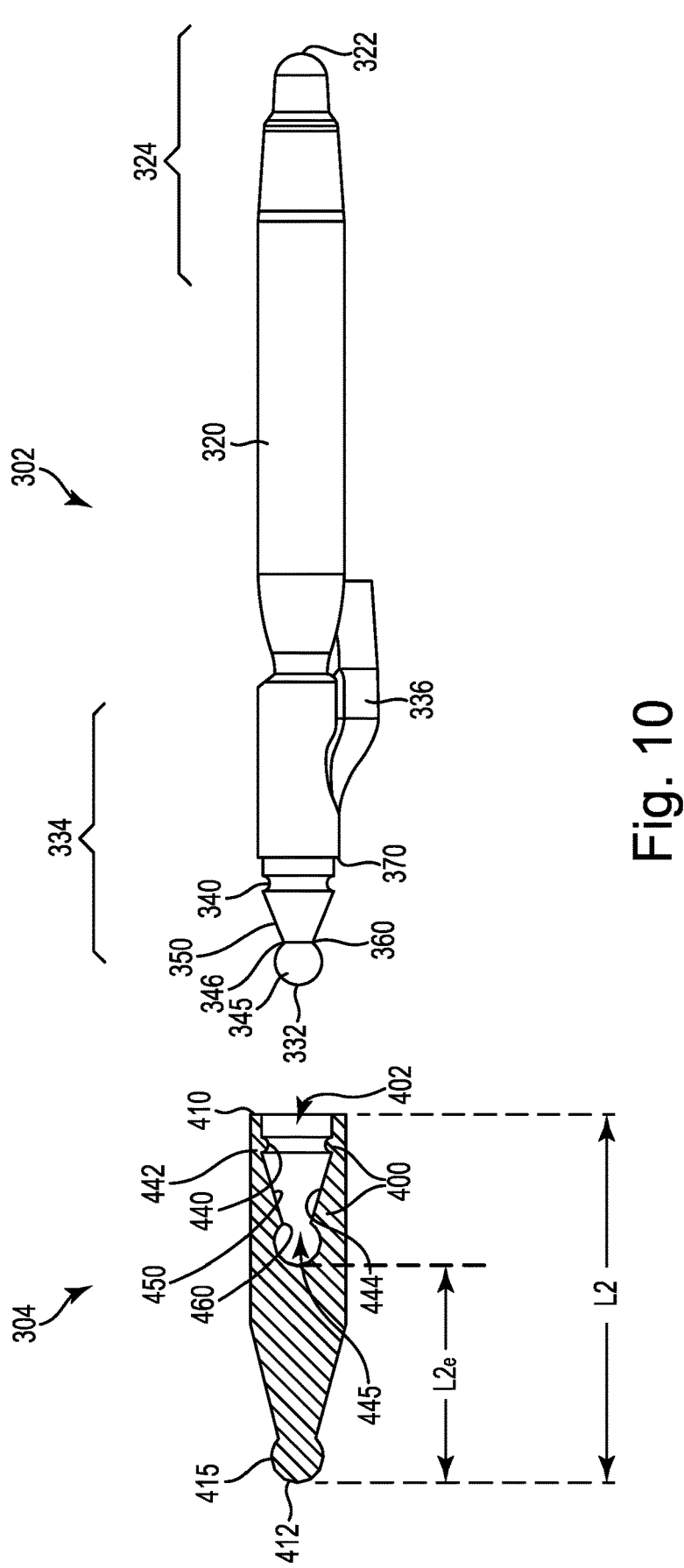
FIG. 10 is a side view of one embodiment of a non-stackable rear tip extender positioned for attachment to a penile implant suitable for use with the system of FIG. 1.

FIG. 10 is a side view of one embodiment of a penile implant 302 suitable for use with the system of FIG. 1 and a non-stackable rear tip extender 304 (non-stackable RTE 304 or RTE 304) attachable to the implant 302. The RTE 304 is referred to as non-stackable because an exterior surface of the RTE 304 is generally smooth. The non-stackable RTE 304 has at most one lock feature provided by a spherical ball 415 at the end of the RTE 304, and the spherical ball 415 is removable (for example by cutting the spherical ball 415 from the RTE 304) to change the effective length of the non-stackable RTE 304. The non-stackable RTE 304 is provided in a variety of lengths and the surgeon selects the single RTE 304 having the specific length the surgeon has determined to best fit the patient and the circumstances. The spherical ball 415 (described below) could be replaced by a non-spherical bulbous shape.

The penile implant 302 includes an inflatable cylinder 320 extending from a distal end 322 of a distal portion 324 of the implant 302 to a proximal-most end 332 of a proximal portion 334 of the penile implant 302. A connection tube 336 is connected to the proximal portion 334 of the penile implant 302, where the connection tube 336 is adapted to couple with the pump 106 and the tubing 110 (FIG. 1) and provide a level of strain relief.

Like embodiments described above, the implant 302 includes two complementary locks in the form of an annular groove 340 and a neck groove 360 formed on either side of a tapered section 350. The proximal portion 334 of the penile implant 302 is formed to include a first sphere 345 that forms the proximal-most end 332 of the penile implant 302 and the neck groove 360 of the penile implant 302 is formed at a junction 346 located between the first sphere 345 and the tapered section 350. The implant 302 includes a step section 370 provided to receive a distal end of the RTE 304; the step section 370 is sized to ensure a smooth planar transition between the RTE 304 and the implant 302, when coupled together.

The annular groove 340 and the neck groove 360 of the implant 302 provide engagement locations that allow durable connection with the RTE 304, and in a complementary manner, an interior of the RTE 304 is provided with a plurality of locks 400 that engage with the annular groove 340 and the neck groove 360. The plurality of locks 400 inside the RTE 304 and the multiple engagement locations 340, 360, 370 on the exterior of the proximal portion 334 of the penile implant 302 combine to provide a durable lock between the two components that resist separation of the RTE 304 from the implant 302, even during an explant procedure.

The RTE 304 extends a length L2 between a distal end 410 and a proximal-most end 412 and is configured to add an effective length L2e when connected with a penile implant. The RTE 304 forms an internal cavity 402 on an interior side that is opposite an exterior side of the RTE 304 that provides a second sphere 415 that forms the proximal-most end 412. In one embodiment, the RTE 304 is a generally cylindrical shaped body formed around the cavity 402 with a larger diameter at the distal end 410 and a smaller diameter at the proximal end 412. The added effective length L2e is measured between a proximal end of the internal cavity 402 to the proximal-most end 412. Multiple stackable RTEs 304 could be packaged in a kit to provide the surgeon with a selection of differently sized RTEs 304 having 0.5 cm incremental added effective lengths L2e.

The plurality of locks 400 include a distal lock 440 and a proximal lock 460. The distal lock 440 is formed as an annular protrusion 442 extending radially inward away from an interior wall 444 of the cavity 402. The annular protrusion 442 is sized to engage in a complementary way with the annular groove 340 of the penile implant 302.

The proximal lock 460 is formed as a wedge-shaped tooth extending radially inward away from the interior wall 444 of the cavity 402, where the wedge-shaped tooth is sized to engage the neck groove 360 of the penile implant 302. The wedge-shaped tooth of the proximal lock 460 is formed at a location where an interior surface of a spherical portion 445 of the cavity 402 meets a tapered section 450 of the interior wall 444 and is an annular wedge-shaped tooth 460. The proximal lock 460 is suitably molded as an integral part of the RTE 304 between the spherical portion 445 and the annular protrusion 402 of the interior wall 444. The spherical portion 445 could be replaced by a non-spherical cavity shape that is sized to receive the non-spherical bulbous shape 345.

The spherical portion 445 of the cavity 402 is sized to receive the first sphere 345 of the proximal portion 334 of the penile implant 302, and the wedge-shaped tooth of the proximal lock 460 of the RTE 304 is adapted to engage the junction 346 formed between the first sphere 345 and the tapered section 350 of the implant 302.

The RTE 304 extends a length L2 between the distal end 410 and the proximal-most end 412, and one suitable length for L2 is provided in a range from about 1 cm to about 5 cm. In one embodiment, the second sphere 415 has a sphere diameter of about 5 mm and the surgeon is provided with instructions for removing the second sphere 415 (for example by cutting), which results in the RTE 304 having an effective length that is 5 mm (or a half centimeter) shorter than the originally sized L2 of the RTE 304. Thus, the RTE 304 is customizable to an effective length in a range from about 0.5 cm to about 4.5 cm.

Figure 11:
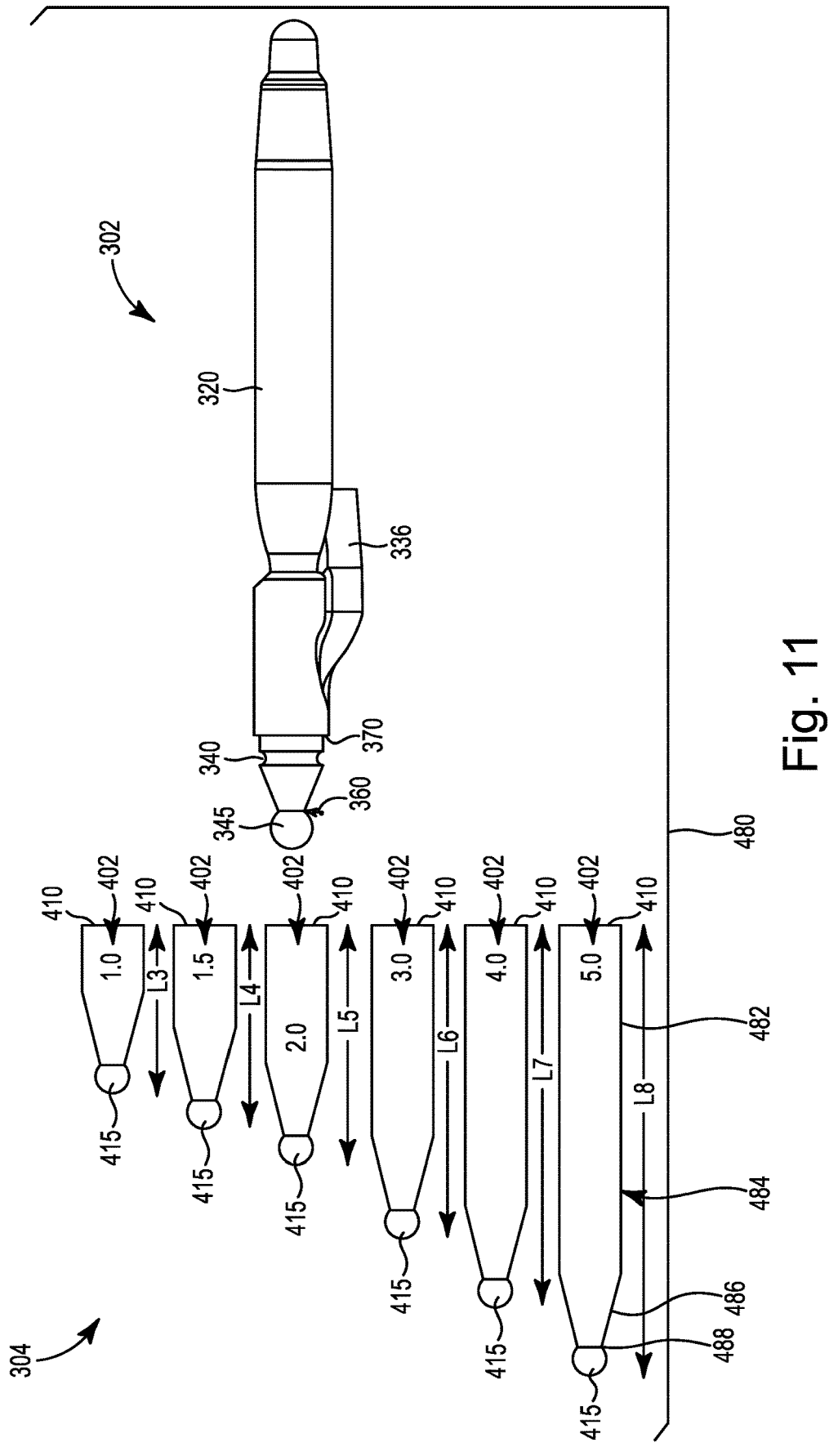
FIG. 11 is a side view of multiple non-stackable rear tip extenders each individually suitable for attachment to a penile implant.

FIG. 11 is a side view of a plurality (for example, six RTEs 304) of non-stackable rear tip extenders RTEs 304 each individually suitable for attachment to the penile implant 302. Each of the non-stackable RTEs 304 has the cavity 402 identified in FIG. 11, where the cavity 402 mates with the plurality of locks 400 (the distal lock 440 and the proximal lock 460).

Each of the non-stackable RTEs 304 is provided with a length L3, L4, L5, L6, L7, and L8, as examples, with L3<L4<L5<L6<L7<L8. The non-stackable RTEs 304 are sized so that each one of the non-stackable RTEs 304 provides the surgeon a different half-centimeter (0.5 cm) incremental added effective length L2e (FIG. 10). In one embodiment, the implant 302 is provided with a selection of different length non-stackable RTEs 304 packaged together in a kit of parts 480 with instructions for use.

During an implant procedure the surgeon may discover that one or both proximal crus penis recesses in the patient are fibrotic or otherwise blocked or possibly longer than expected. The surgeon will measure each crus penis and select an appropriate one of the different length non-stackable RTEs 304 and attach it to the implant 302 by engaging the cavity 402 of the RTE 304 with the proximal portion 334 of the implant 302 (FIG. 10). As noted above, each of the different length non-stackable RTEs 304 includes the second sphere 415 that is suited for placement at the proximal location of the crus penis. Alternatively, the second sphere 415 of the non-stackable RTE 304 may be removed by cutting to adjust the effective length of the selected RTE 304 by an approximately 5 mm increment. In this manner, the kit of parts 480 allows the surgeon to select and accurately provide a suitably sized implant 302/RTE 304 for most patient conditions encountered during most surgeries.

The interior surface of the RTE is provided with the plurality of locks 400 and an exterior surface of the non-stackable RTE 304 is characterized by an absence of multiple locking features. Thus, a single non-stackable RTE 304 may be connected to the implant 302 to adjust the length of the implant 302, but an additional one of the non-stackable RTE 304 is not suited for attachment to an attached RTE 304, and this is what is meant by non-stackable RTE 304.

The non-stackable RTE 304 has an exterior wall 482 having a cylindrical section 484 extending from the distal end 410 in a direction toward the second sphere 415 at the proximal-most end, a tapered RTE section 486 proximal the cylindrical section 484, with the tapered RTE section 486 having a continuous reduction in diameter from the cylindrical section 484 to the second sphere 415, and a neck RTE groove 488 formed in the tapered RTE section 486 at a junction of the second sphere 415 and the tapered RTE section 486. The absence of multiple locking features on the exterior of the non-stackable RTE 304 means that the RTE 304 could be attached to the implant 302, but could also be easily removed, which is not desirable for an implanted rear tip extender that might eventually be explanted.

Figure 12:
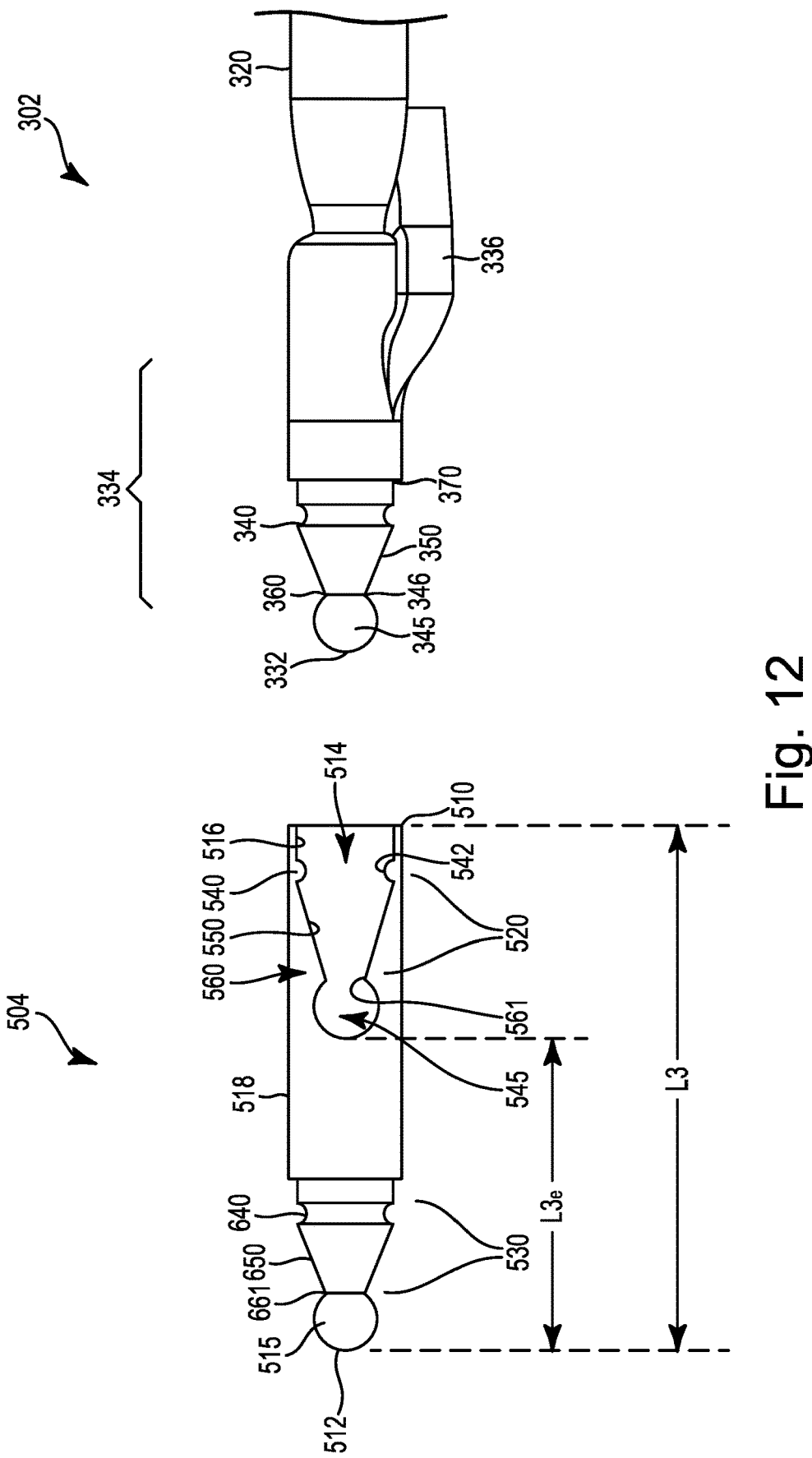
FIG. 12 is a side view of one embodiment of a stackable rear tip extender positioned for attachment to a penile implant suitable for use with the system of FIG. 1.

FIG. 12 is a side view of one embodiment of a stackable rear tip extender 504 (stackable RTE 504 or RTE 504) attachable to the implant 302 and suitable for use with the system of FIG. 1.

Like the embodiments described above, the implant 302 includes two complementary locks in the form of the annular groove 340 and the neck groove 360 formed on either side of the tapered section 350. The proximal portion 334 of the penile implant 302 is formed to include the first sphere 345 that forms the proximal-most end 332 of the penile implant 302 and the neck groove 360 of the penile implant 302 is formed at the junction 346 between the first sphere 345 and the tapered section 350. The step section 370 is provided to receive the distal end of the RTE 504, where the step section 370 is sized to ensure a smooth planar transition between the RTE 504 and the implant 302.

In this embodiment, the interior surface of the RTE 504 is provided with a plurality of locks and an exterior surface of the stackable RTE 504 is provided with multiple locking features. Thus, each stackable RTE 504 may be connected to the proximal portion 334 of the implant 302 or connected to another already attached stackable RTE 504, and this allows stacking RTEs 504 together to arrive at a specific selected effective length for the implant.

The RTE 504 extends a length L3 between a distal end 510 and a proximal-most end 512 and is configured to add an effective length L3e when connected with a penile implant. The RTE 504 forms an internal cavity 514 formed by an interior wall 516 that is opposite an exterior surface 518 of the RTE 504. The exterior surface 518 of the RTE 504 includes a second sphere 515 that forms the proximal-most end 512 of the RTE 504. In one embodiment, the RTE 504 is a generally cylindrical shape formed around the cavity 514 with a larger diameter at the distal end 510 and a smaller diameter at the proximal end 512 and the second sphere 515. The added effective length L3e is measured between a proximal end of the internal cavity 514 to the proximal-most end 512. Multiple stackable RTEs 504 could be packaged in a kit to provide the surgeon with a selection of differently sized RTEs 504 having 0.5 cm incremental added effective lengths L3e.

The RTE 504 is formed to have a plurality of locks 520 inside the cavity 514 and a plurality of locks 530 formed on the exterior wall 518.

The plurality of locks 520 inside the cavity 514 include a distal lock 540 and a proximal lock 560.

The distal lock 540 is formed as an annular protrusion 542 extending radially inward away from the interior wall 516 of the cavity 514. The annular protrusion 542 is sized to engage in a complementary way with the annular groove 340 of the penile implant 302.

The proximal lock 560 is formed as a wedge-shaped tooth 561 extending radially inward away from the interior wall 516 of the cavity 514, where the wedge-shaped tooth 561 is sized to engage the neck groove 360 of the penile implant 302. The wedge-shaped tooth 561 of the proximal lock 560 is formed at a location where an interior surface of a spherical portion 545 of the cavity 514 meets a tapered section 550 of the interior wall 516 and is an annular wedge-shaped tooth 461.

The spherical portion 545 of the cavity 514 is sized to receive the first sphere 345 of the proximal portion 334 of the penile implant 302, and the wedge-shaped tooth 561 of the proximal lock 560 of the RTE 504 is adapted to engage the junction 346 formed between the first sphere 345 and the tapered section 350 of the implant 302.

One suitable added effective length L3e for the RTE 504 is in a range from about 1 cm to about 5 cm. In one embodiment, the second sphere 515 has a sphere diameter of about 5 mm and the surgeon is provided with instructions for removing the second sphere 515 (for example by cutting), which results in the RTE 504 having an added effective length L3e that is 5 mm (or a half centimeter) shorter than the originally sized RTE 504. Thus, the RTE 504 is customizable to an added effective length L3e in a range from about 0.5 cm to about 4.5 cm.

The exterior wall 518 of the stackable RTE 504 includes an annular RTE groove 640 formed around a circumference of the stackable RTE 504, a tapered RTE section 650 proximal the annular RTE groove 640, with the tapered RTE section 650 having a continuous reduction in diameter from the annular RTE groove 640 toward the second sphere 515 at the proximal-most end 512 of the stackable RTE 504, and a neck RTE groove 661 formed in the tapered RTE 650 section at a junction between the second sphere 515 and the tapered RTE section 650.

Thus, the plurality of locks 530 formed on the exterior wall 518 include portions of the annular RTE groove 640, the tapered RTE section 650, the second sphere 515, and the neck RTE groove 661. The RTE 504 is a stackable rear tip extender because each annular RTE groove 640 is adapted to engage with the annular protrusion 542 of another RTE 504; the tapered RTE section 650 is adapted to engage with the tapered section 550 of another RTE 504; the second sphere 515 is adapted to fit inside of the spherical portion 545 of the cavity 514; and the neck RTE groove 661 is adapted to engage with the wedge-shaped tooth 561 formed inside the cavity 514.

FIG. 13 is a side view of multiple stackable rear tip extenders 504a, 504b, 504c each suitable for attachment to each other and suitable for attachment to the penile implant 302.

The plurality of the stackable RTEs 504a, 504b, 504c each has the exterior wall 518 formed to include the annular RTE groove 640, the tapered RTE section 650, and the neck RTE groove 661. In one embodiment, each one of the plurality of the stackable RTEs 504a, 504b, 504c provides an added effective length L3e that is different from an added effective length L3e of another one of the plurality of the stackable RTEs. In one example, the added effective length L3e of RTE 504a is less than the added effective length L3e of RTE 504b, and the added effective length L3e of RTE 504b is less than the added effective length L3e of RTE 504c. One suitable added effective length L3e for RTE 504a is about 1.5 cm; one suitable added effective length L3e for RTE 504b is about 2.0 cm; and one suitable added effective length L3e for RTE 504c is about 3.0 cm. Each sphere 515 of each RTE 504 is removable by cutting to reduce an effective length of each RTE 504 by about 5 mm, which the surgeon might find helpful when accurately sizing a final length of an implant for a patient.

Although specific embodiments have been illustrated and described herein, it will be appreciated by those of ordinary skill in the art that a variety of alternate and/or equivalent implementations may be substituted for the specific embodiments shown and described without departing from the scope of the present invention. This application is intended to cover any adaptations or variations of medical devices as discussed herein.

What is claimed is:

1. An implantable penile prosthesis system comprising:
a penile implant comprising a proximal portion implant-able in a crus penis, with the proximal portion of the penile implant comprising:
an annular groove formed around a circumference of the penile implant to define a groove diameter,
a tapered section proximal the annular groove, with the tapered section having a continuous reduction in diameter from the annular groove toward a proximal-most end of the penile implant,
a neck groove formed in the tapered section between the proximal-most end of the penile implant and the annular groove; and
a rear tip extender forming a cavity sized to receive the proximal portion of the penile implant, with the cavity defined by an interior wall provided with a plurality of locks comprising:
a distal lock formed as an annular protrusion extending radially inward away from the interior wall of the cavity, where the annular protrusion is sized to engage with the annular groove of the penile implant, and
a proximal lock formed as a wedge-shaped tooth extending radially inward away from the interior wall of the cavity, with the wedge-shaped tooth sized to engage the neck groove of the penile implant.

2. The system of claim 1, wherein the annular protrusion of the distal lock is sized to engage with an entire circum-ference of the annular groove of the penile implant, and the proximal lock comprises a plurality of wedge-shaped teeth extending radially inward away from the interior wall of the cavity, with the plurality of wedge-shaped teeth distributed around a circumference of the cavity of the rear tip extender.

3. The system of claim 1, wherein the annular protrusion of the distal lock is sized to engage with an entire circum-ference of the annular groove of the penile implant, and the wedge-shaped tooth of the proximal lock is sized to engage with an entire circumference of the neck groove of the penile implant.

4. The system of claim 1, wherein the proximal portion of the penile implant further comprises a step section distal the annular groove, with the step section having a step diameter that is greater than the groove diameter;
wherein, when the rear tip extender is coupled to the proximal portion of the penile implant, an exterior surface of the rear tip extender smoothly transitions and is co-planar to an exterior surface of the proximal portion of the penile implant.

5. The system of claim 1, wherein a joint is formed at a location where the rear tip extender is coupled to the proximal portion of the penile implant, and the plurality of locks of the rear tip extender combine to prevent formation of a gap in the joint when a bending force is applied to the system.

6. The system of claim 1, wherein the neck groove of the proximal portion of the penile implant is formed by a junction between a portion of a spherical ball attached proximal to the tapered section, and the wedge-shaped tooth is sized to engage with the junction.

7. The system of claim 1, wherein the neck groove of the proximal portion of the penile implant is formed by a junction between a portion of a spherical ball attached proximal to the tapered section, and a diameter of the portion of the spherical ball is larger than a smallest diameter of the tapered section.

8. The system of claim 7, wherein the cavity of the rear tip extender includes a section of a spherical cavity located proximal to the wedge-shaped tooth and sized to receive the portion of the spherical ball.

9. The system of claim 1, wherein the penile implant is an inflatable penile implant attachable to a liquid reservoir and a pump by tubing.

10. The system of claim 1, wherein the proximal portion of the penile implant further comprises a first sphere that forms the proximal-most end of the penile implant and the neck groove of the penile implant is formed at a junction between the first sphere and the tapered section.

11. The system of claim 10, wherein the cavity of the rear tip extender is formed to include a spherical cavity sized to receive the first sphere of the proximal portion of the penile implant, and the wedge-shaped tooth of the proximal lock on the interior wall of the rear tip extender is formed by a surface of the spherical cavity and is adapted to engage the junction located between the first sphere and the tapered section.

12. The system of claim 10, wherein the rear tip extender further comprises a second sphere that forms a proximal-most end of the rear tip extender.

13. The system of claim 12, wherein the rear tip extender comprises a stackable rear tip extender (RTE), with an exterior wall of the stackable RTE comprising:
an annular RTE groove formed around a circumference of the stackable RTE,
a tapered RTE section proximal the annular RTE groove, with the tapered RTE section having a continuous reduction in diameter from the annular RTE groove toward the second sphere at the proximal-most end of the stackable RTE, and
a neck RTE groove formed in the tapered RTE section at a junction between the second sphere and the tapered RTE section.

14. The system of claim 13, further comprising a plurality of the stackable RTEs, with the exterior wall of each of the plurality of the stackable RTEs comprising the annular RTE groove, the tapered RTE section, and the neck RTE groove.

15. The system of claim 14, wherein each one of the plurality of the stackable RTEs has a length that is different from a length of an other one of the plurality of the stackable RTEs.

16. The system of claim 12, wherein the rear tip extender comprises a non-stackable rear tip extender (RTE), with an exterior wall of the non-stackable RTE comprising:

a cylindrical section extending from a distal end of the non-stackable RTE in a direction toward the proximal-most end of the non-stackable RTE, a tapered RTE section proximal the cylindrical section, with the tapered RTE section having a continuous reduction in diameter from the cylindrical section to the second sphere at the proximal-most end of the non-stackable RTE, and a neck RTE groove formed in the tapered RTE section at a junction of the second sphere and the tapered RTE section.

17. The system of claim 16, further comprising a plurality of the non-stackable RTEs.

18. The system of claim 17, wherein each one of the plurality of the non-stackable RTEs has a length of the cylindrical section that is different from a length of the cylindrical section of an other one of the plurality of the non-stackable RTEs.

19. An implantable penile prosthesis system comprising:

a penile implant comprising a proximal portion implantable in a crus penis, with the proximal portion of the penile implant comprising:

an annular groove formed around a circumference of the penile implant to define a groove diameter, a tapered section proximal the annular groove, with the tapered section having a continuous reduction in diameter from the annular groove toward a proximal-most end of the penile implant, a neck groove formed in the tapered section between the proximal-most end of the penile implant and the annular groove; and a rear tip extender forming a cavity sized to receive the proximal portion of the penile implant, with the cavity defined by an interior wall provided with a plurality of locks comprising:

a distal lock formed as an annular protrusion extending radially inward away from the interior wall of the cavity, where the annular protrusion is sized to engage with the annular groove of the penile implant, and a proximal lock formed as a plurality of wedge-shaped teeth extending radially inward away from the interior wall of the cavity, with the plurality of wedge-shaped teeth distributed around a circumference of the cavity of the rear tip extender.

\* \* \* \* \*